(12) United States Patent
Tai

(10) Patent No.: US 10,281,370 B2
(45) Date of Patent: May 7, 2019

(54) SYRINGE ASSEMBLY AND METHOD OF USING THE SAME

(71) Applicant: TAIGEN BIOSCIENCE CORPORATION, Taipei (TW)

(72) Inventor: Chi-Sheng Tai, Taipei (TW)

(73) Assignee: TAIGEN BIOSCIENCE CORPORATION, Taipei (TW)

(*) Notice: Subject to any disclaimer, the term of this patent is extended or adjusted under 35 U.S.C. 154(b) by 224 days.

(21) Appl. No.: 15/487,251

(22) Filed: Apr. 13, 2017

(65) Prior Publication Data

US 2017/0307481 A1 Oct. 26, 2017

(30) Foreign Application Priority Data

Apr. 26, 2016 (TW) .............................. 105112944 A

(51) Int. Cl.
*B01L 3/02* (2006.01)
*G01N 1/14* (2006.01)
(Continued)

(52) U.S. Cl.
CPC .............. *G01N 1/14* (2013.01); *B01L 3/0217* (2013.01); *G01F 11/006* (2013.01);
(Continued)

(58) Field of Classification Search
CPC ............. B01L 3/0217; B01L 2200/026; B01L 2200/143; B01L 2300/0627; B01L 2400/0478; G01F 11/006; G01F 25/0092; G01F 22/00; G01F 23/296; G01N 1/14; G01N 35/1016; G01N 2001/1427; G01N 2035/1025

See application file for complete search history.

(56) References Cited

U.S. PATENT DOCUMENTS

| 4,846,003 A | * | 7/1989 | Marquiss | .............. B01L 3/0275 |
|---|---|---|---|---|
| | | | | 73/864.24 |
| 4,864,856 A | * | 9/1989 | Ichikawa | ............ G01F 23/2966 |
| | | | | 73/290 V |

(Continued)

FOREIGN PATENT DOCUMENTS

| JP | 04077670 A | * | 3/1992 |
|---|---|---|---|
| KR | 20090067446 A | * | 6/2009 |

(Continued)

OTHER PUBLICATIONS

Machine translation of KR 20090067446-A which originally published on Jun. 2009.*

*Primary Examiner* — David A Rogers
(74) *Attorney, Agent, or Firm* — Cheng-Ju Chiang

(57) ABSTRACT

The disclosure relates to a syringe assembly and a syringing method of using the same. The syringe assembly comprises an ultrasonic element, a guide tube and a syringe. The ultrasonic element is used to generate an ultrasonic signal and receive a reflection of the ultrasonic signal. The guide tube comprises a first connecting terminal and a second connecting terminal. The syringe and the guide tube are connected with each other via the second connecting terminal. The syringe assembly according to the present disclosure is able to perform sampling, liquid level detection, clog detection, and the liquid volume detection.

10 Claims, 3 Drawing Sheets

(51) Int. Cl.
*G01F 11/00* (2006.01)
*G01F 22/00* (2006.01)
*G01F 25/00* (2006.01)
*G01N 35/10* (2006.01)
*G01F 23/296* (2006.01)

(52) U.S. Cl.
CPC ..... *G01F 25/0092* (2013.01); *G01N 35/1016* (2013.01); *B01L 2200/026* (2013.01); *B01L 2200/143* (2013.01); *B01L 2300/0627* (2013.01); *B01L 2400/0478* (2013.01); *G01F 22/00* (2013.01); *G01F 23/296* (2013.01); *G01N 2001/1427* (2013.01); *G01N 2035/1025* (2013.01)

(56) References Cited

U.S. PATENT DOCUMENTS

| | | | | |
|---|---|---|---|---|
| 5,311,871 A | * | 5/1994 | Yock | A61B 8/0833 600/461 |
| 5,465,629 A | * | 11/1995 | Waylett, Jr. | G01F 23/2962 73/864.16 |
| 5,648,727 A | | 7/1997 | Tyberg et al. | |
| 5,693,292 A | * | 12/1997 | Choperena | G01N 35/0092 422/63 |
| 5,705,750 A | * | 1/1998 | Mizukami | G01F 23/2962 222/420 |
| 5,855,851 A | * | 1/1999 | Matsubara | G01F 23/263 141/130 |
| 5,906,795 A | * | 5/1999 | Nakashima | B01L 3/0275 422/509 |
| 7,191,647 B2 | * | 3/2007 | Harazin | G01F 23/26 340/620 |
| 7,823,447 B2 | * | 11/2010 | Harazin | G01F 23/266 73/304 R |
| 7,836,763 B2 | * | 11/2010 | Harazin | G01F 23/26 340/620 |
| 8,100,007 B2 | | 1/2012 | Elsenhans et al. | |
| 8,287,806 B2 | | 10/2012 | Bjornson et al. | |
| 8,435,464 B2 | * | 5/2013 | Zuppiger | B01L 3/021 422/501 |
| 8,726,745 B2 | * | 5/2014 | Heinze | G01F 23/2962 422/501 |
| 9,733,115 B2 | * | 8/2017 | Endo | G01F 23/00 |
| 9,861,756 B1 | * | 1/2018 | Krasnow | A61M 5/31568 |
| 2005/0092080 A1 | * | 5/2005 | Harazin | G01F 23/26 73/290 R |
| 2005/0124059 A1 | * | 6/2005 | Kureshy | G01N 35/1011 435/287.2 |
| 2007/0012113 A1 | * | 1/2007 | Ulmer | G01F 23/2962 73/618 |
| 2017/0173576 A1 | * | 6/2017 | Natsume | B01L 3/0237 |

FOREIGN PATENT DOCUMENTS

TW 200502545 A 1/2005
TW I422801 B 1/2014

* cited by examiner

SYRINGE ASSEMBLY AND METHOD OF USING THE SAME

FIELD OF THE INVENTION

The present invention relates to a syringe assembly and a method of using the same, and in particular, is applied for automated sampling equipments in the biomedical industry.

BACKGROUND OF THE INVENTION

In a biomedical laboratory, usually a volumetric pipette is adopted to quantitatively sample and transfer the liquid specimens. However, in order to avoid cross-contamination among the specimens, the volumetric pipette is capped with a disposable sampling head (as so-called "tip"). Basically, the sampling head can be used only for one time. A principle of the volumetric pipette in operation is that the specimen enters into the sampling head by vacuum method; and likewise, the specimen is outlet from the sampling head by a thrust force generated by the vacuum method. Generally, a main body of the sampling head is shaped cylindrical with converging to a tapered opening at its bottom.

A liquid specimen sampled for a biomedical laboratory includes, for example, a serum, plasma and whole blood, which contains a large amount of protein, carbohydrate, fat, blood cell, cell, and microorganism such that the liquid specimen belongs to a viscous liquid which contains particles and/or colloid substances. Therefore, a manner of operating the tapered opening of the sampling head on an accurately-and-correctly quantitative sampling exists a certain level of difficulty. In manual operation, the operator can avoid "clog" from the particles and/or colloid substances by instant human-eye observation on inspecting whether a volume of the suctioned/discharged specimen is correct or not, or can immediately stop suction/discharge to avoid contaminating the volumetric pipette when the "clog" occurs.

Basically, the accuracy and correctness of specimen suction/discharge are very important. If the correctness of the specimen suction/discharge could not be ensured, this might invoke false negatives or false positives, thereby resulting in misjudgment of the experimental results.

In the conventional art, the automated equipment has several following problems that include: 1. liquid level detection; 2. clog detection; and 3. volume detection.

For the liquid level detection, the volumetric pipette is able to detect the liquid level of the specimen for suction/discharge depending on the position of the liquid surface. This can prevent the sampling head from entering under the liquid surface of the specimen, and to dip too much of the specimen to generate carry-over and cross contamination matters.

For the clog detection, in the manner that the volumetric pipette could not be detected in time but continue to suction when the tapered opening of the sampling head is blocked, it will cause the internal pressure of the sampling head to be abnormal. When a clogging is suctioned into the sampling head, the specimen may be ejected into the inside of the volumetric pipette due to the pressure, thereby contaminating the volumetric pipette and thereby affecting subsequent sampling.

For volume detection, the suctioned specimen needs to be fixed whereby it is important to detect the volume of each sampled specimen, especially for use in the automated equipment.

However, in the automated equipment, it is urgent to solve the above three technical issues, and to ensure the accuracy and correctness of the specimen suction/discharge without the operator's inspection.

With reference to U.S. Pat. No. 5,648,727, which places a capacitive sensing element on a volumetric pipette in conjunction with an electrically conductive pick-up head, so that when the conductible head is close to the liquid level of the conductible specimen, a current is generated dependent upon the capacitance difference, and then the height of the liquid level is acquired based on calculating the current. However, this method has a problem of detecting errors for a non-conductive specimen or a foamed specimen.

With reference to U.S. Pat. No. 8,287,806, which provides a sensor for detecting a pressure difference, the air inside the suction head is compressed to produce a pressure change when the specimen enters into the suction head. Furthermore, a volume of the specimen within the suction head can be acquired by calculating the pressure difference. However, this method requires a complete air-tightness, which also means a higher cost required. At the same time, once if there is any air leakage, error measurement is inevitable.

With reference to U.S. Pat. No. 8,100,007, the method of this patent includes the steps of: first, to detect the level of the liquid surface of the specimen and then to lower the suction head to the liquid surface of the specimen when the liquid level of the specimen is detected, to absorb the specimen. There is a drawback in that the determination of the volume of the suctioned specimen and the clog judgment could not be simultaneously performed during the suctioning process of the specimen. For the automated equipment, such a drawback would result in several technical problems of contamination of the quantitative pipette and/or other contaminations.

However, the conventional art provides solutions to the above-mentioned technical problems, but there is no effective way to solve the above-mentioned technical problems at the same time.

SUMMARY OF THE INVENTION

In order to solve the aforementioned technical problems of the conventional art, an objective of the present disclosure is to provide a syringe assembly. The present disclosure simultaneously performs sampling, clog detection, liquid surface detection, and liquid volume detection, by a guide tube, which are respectively connected with an ultrasonic element and a syringe at the same time.

In order to achieve the object, the present disclosure provides a syringe assembly, which comprises an ultrasonic element, a guide tube and a syringe.

The ultrasonic element is used for generating an ultrasonic signal and receiving a reflection of the ultrasonic signal. The guide tube comprises a first connecting terminal and a second connecting terminal. The guide tube is connected with the ultrasonic element via the first connecting terminal. The syringe is connected with the guide tube via the second connecting terminal.

In a preferred embodiment, the guide tube further comprises a third connecting terminal for disposing a sampling head (tip) thereon.

In a preferred embodiment, the first connecting terminal and the second connecting terminal are disposed coaxially.

In a preferred embodiment, the first connecting terminal, the second connecting terminal and the third connecting terminal are communicated with each other.

In a preferred embodiment, a waveform convergence hole is located between the first connecting terminal and the third connecting terminal.

In order to achieve the object, the present disclosure provides a syringing method, which comprises the following steps. First, a syringe assembly is putted into a to-be-tested liquid; an ultrasonic element disposed on the syringe assembly continuously emits signals to detect a liquid level located within a sampling head of the syringe assembly; a syringe of the syringe assembly performs a suction procedure to suction the to-be-tested liquid into the sampling head; the liquid level and the suction procedure are simultaneously compared; and when it is determined that the liquid level is not corresponded to the suction procedure, the suction procedure is stopped, immediately.

In a preferred embodiment, the syringe assembly further comprises a guide tube, which includes a first connecting terminal and a second connecting terminal. The guide tube is connected with the ultrasonic element via the first connecting terminal; the syringe is connected with the guide tube via the second connecting terminal.

In a preferred embodiment, the guide tube further comprises a third connecting terminal for disposing a sampling head thereon.

In a preferred embodiment, the first connecting terminal, the second connecting terminal and the third connecting terminal are communicated with each other.

In a preferred embodiment, a waveform convergence hole is located between the first connecting terminal and the third connecting terminal.

Compared with the conventional art, the present disclosure simultaneously performs specimen sampling, clog detection, liquid surface detection, and liquid volume detection, by a guide tube, which is respectively connected with an ultrasonic element and a syringe at the same time.

DETAILED DESCRIPTION OF THE PREFERRED EMBODIMENTS

The following description of the embodiments is given by way of illustration with reference to the specific embodiments in which the disclosure may be practiced. The terms such as "up", "down", "front", "back", "left", "right", "inside", "outside", "side", etc. The direction of the diagram. Accordingly, the use of directional terms is used to describe and to understand the present disclosure and is not intended to limit the disclosure.

Figure 1:
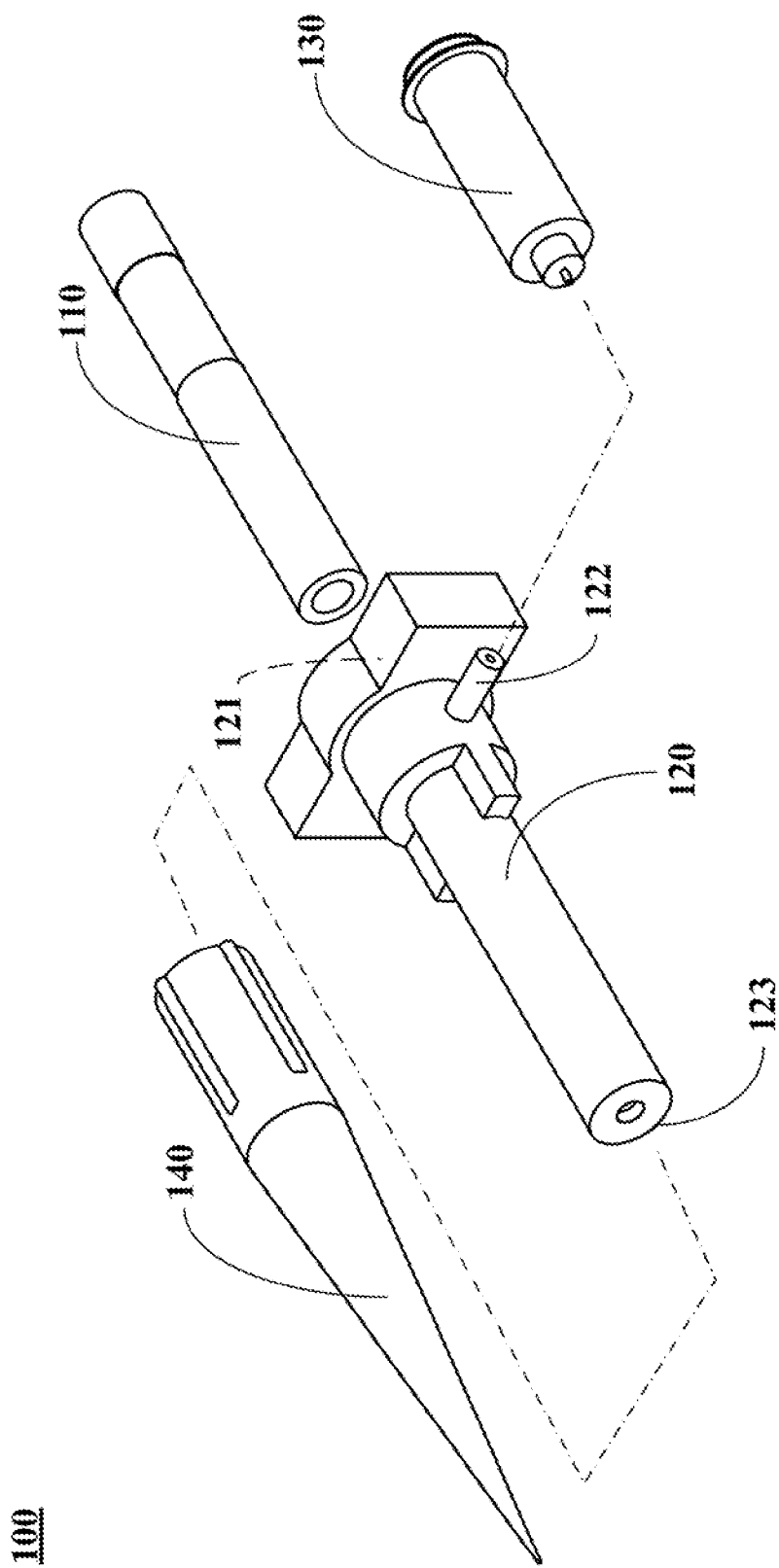
FIG. 1 depicts a disassemble view of a syringe assembly according to the present disclosure.
Figure 2:
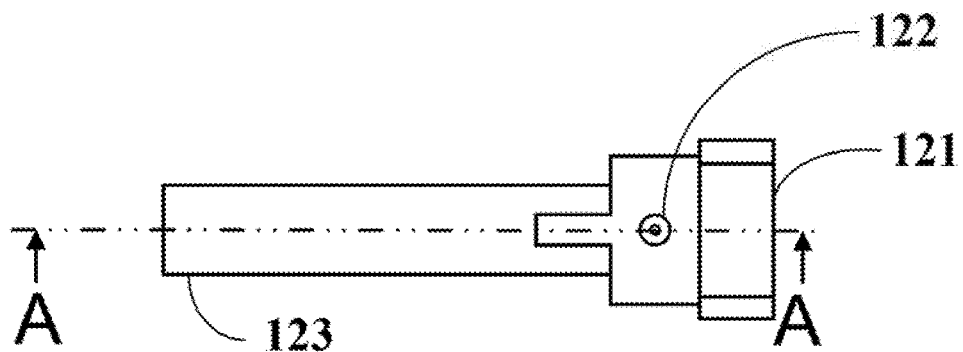
FIG. 2 depicts a top view of the guide tube of FIG. 1.
Figure 3:
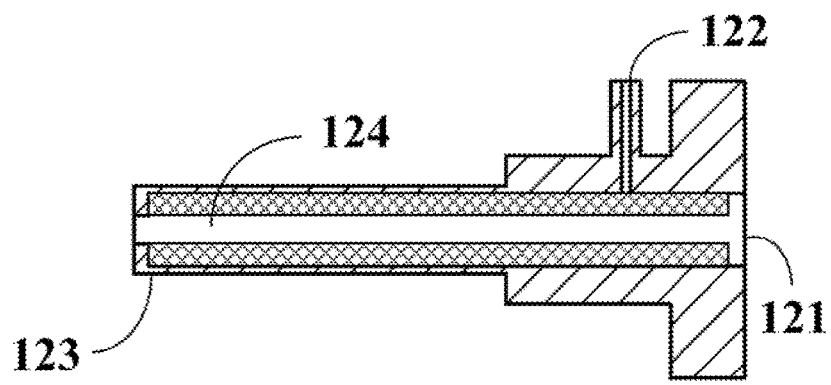
FIG. 3 depicts a cross-sectional view along line A-A' of the guide tube of FIG. 2.

Please refer to FIGS. 1-3. FIG. 1 depicts a disassemble view of a syringe assembly 100 according to the present disclosure. FIG. 2 is a top view of the guide tube 120 of FIG. 1. FIG. 3 is a cross-sectional view along line A-A' of the guide tube 120 of FIG. 2. The syringe assembly 100 comprises an ultrasonic element 110, a guide tube 120, a syringe 130 and a sampling head 140.

The ultrasonic element 110 is used to generate an ultrasonic signal and receive a reflection of the ultrasonic signal. In detail, the liquid surface level of a to-be-tested liquid can be acquired by the ultrasonic signal. So that the volume of the to-be-tested liquid can be derived by calculation dependent upon the liquid surface level. The guide tube 120 comprises a first connecting terminal 121, a second connecting terminal 122 and a third connecting terminal 123. In detail, the syringe 130 sucks a specimen into the sampling head 140 by a pressure difference. The guide tube 120 is connected with the ultrasonic element 110 via the first connecting terminal 121. The syringe 130 is connected with the guide tube 120 via the second connecting terminal 122. The third connecting terminal 123 is used for disposing the sampling head 140 thereon.

Preferably, in an automated equipment, the syringe 130 is automatically performed on suction/discharge of the specimen, according to a command of computer equipment.

Preferably, the first connecting terminal 121 and the ultrasonic element 110 can be fixed by thread, latch etc. The second connecting terminal 122 and the syringe 130 can be connected with each other by a rubber structure.

In actual practice, the first connecting terminal 121 and the second connecting terminal 122 are disposed coaxially, in order to emit the ultrasonic signal of the ultrasonic element 110 to the liquid surface of the specimen within the sampling head 140, for more precisely determining the level of the liquid surface of the specimen within the sampling head 140.

In detail, the first connecting terminal 121, the second connecting terminal 122 and the third connecting terminal 123 are communicated with each other. That is because the first connecting terminal 121 and the third connecting terminal 123 are communicated with each other for transmitting the ultrasonic signal between the first connecting terminal 121 and the third connecting terminal 123. And the second connecting terminal 122 and the third connecting terminal 123 are communicated with each other for suctioning the specimen by a pressure difference generated from the syringe 130. Furthermore, a waveform convergence hole 124 is formed and located between the first connecting terminal 121 and the third connecting terminal 123; the waveform convergence hole 124 can make the waveform of the ultrasonic signal much more suitable for detecting the level of the liquid surface of the specimen.

Actually, after the syringe assembly 100 is disposed on an automated equipment (not shown), the syringe 130 starts to suction the specimen into inside of the sampling head 140; and meanwhile, the ultrasonic element 110 continuously emits the ultrasonic signal to detect the liquid level of the specimen within the sampling head 140. Because the syringe 130 and the ultrasonic element 110 both are respectively connected with the automated equipment, the automated equipment can determine whether the volume of the specimen within the sampling head 140 (based on the calculation of the liquid level) and the volume of the specimen suctioned by the syringe 130 are consistent or not, so as to further determine whether clog occurred or not. The present disclosure achieves the technical effect of simultaneously clog detection by suctioning the specimen and detecting the liquid level of the specimen at the same time.

Figure 4:
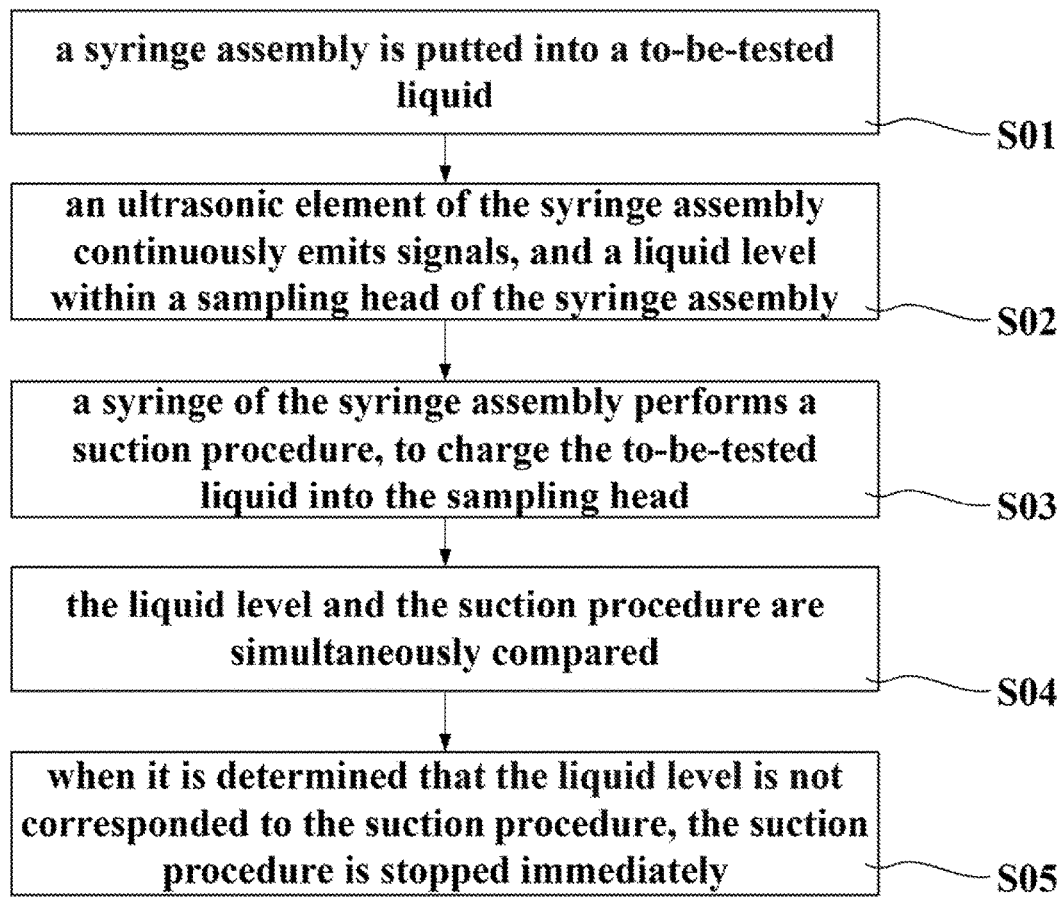
FIG. 4 depicts a flow diagram of the syringing method according to the present disclosure.

FIG. 4 is a flow diagram of the present disclosure. The elements used in the present disclosure are referred to FIGS. 1-3. First, step S01, a syringe assembly 100 is putted into a to-be-tested liquid; step S02, an ultrasonic element 110 of the syringe assembly 100 continuously emits signals to detect a liquid level located within a sampling head 140 of the syringe assembly 100; step S03, a syringe 130 of the syringe assembly 100 is performed on a suction procedure to suction the to-be-tested liquid into the sampling head 140;

step S04, the liquid level and the suction procedure are simultaneously compared with each other; and step S05, when it is determined that the liquid level is not corresponded to the suction procedure, the suction procedure is stopped, immediately.

In detail, the suction procedure includes the automated equipment setting the quantity of specimens to be suctioned (ex. Volume) and driving the syringe 130 to carry out the suction procedure (i.e., sampling action); likewise, the liquid surface and the suction procedure are simultaneously compared with each other by the automated equipment. When the liquid level is not corresponded to the suction procedure, it means that the set quantity of specimens does not coincide with the number of specimens within the sampling head 140. For example, comparing a liquid level of 2 c.c. suctioned by the syringe 130 with a liquid level of only 1.95 c.c. within the sampling head 140 indicates that a clog problem may occur whereby the suction procedure should be stopped, and then the clog problem can be solved manually or the automated equipment will perform subsequent procedures.

While the foregoing are merely preferred embodiments of the present disclosure, it should be noted that those skilled in the art will appreciate that modifications and improvements may be made without departing from the principles of the disclosure, the modifications and improvements should be regarded with the scope of the present disclosure.

As described above, although the present disclosure has been described with the preferred embodiments thereof, those skilled in the art will appreciate that various modifications, additions, and substitutions are possible without departing from the scope and the spirit of the disclosure. Accordingly, the scope of the present disclosure is intended to be defined only by reference to the claims.

What is claimed is:

1. A syringe assembly, comprising:
   an ultrasonic element generating an ultrasonic signal and receiving a reflection of the ultrasonic signal;
   a guide tube comprising a first connecting terminal and a second connecting terminal, the guide tube connecting with the ultrasonic element via the first connecting terminal; and
   a syringe connecting with the guide tube via the second connecting terminal.

2. The syringe assembly according to claim 1, wherein the first connecting terminal and the second connecting terminal are disposed coaxially.

3. The syringe assembly according to claim 1, wherein the guide tube further comprises a third connecting terminal for disposing a sampling head thereon.

4. The syringe assembly according to claim 3, wherein the first connecting terminal, the second connecting terminal and the third connecting terminal are communicated with each other.

5. The syringe assembly according to claim 3, wherein a waveform convergence hole is located between the first connecting terminal and the third connecting terminal.

6. A syringing method, comprising:
   putting a syringe assembly into a to-be-tested liquid;
   continuously emitting signals by an ultrasonic element of the syringe assembly, to detect a liquid level within a sampling head of the syringe assembly;
   performing a suction procedure by a syringe of the syringe assembly, suctioning the to-be-tested liquid into the sampling head; and
   simultaneously comparing the liquid level with the suction procedure;
   wherein when it is determined that the liquid level is not corresponded to the suction procedure, the suction procedure is stopped, immediately.

7. The syringing method according to claim 6, wherein the syringe assembly further comprises a guide tube, which includes a first connecting terminal and a second connecting terminal, and the guide tube is connected with the ultrasonic element via the first connecting terminal, and the syringe is connected with the guide tube via the second connecting terminal.

8. The syringing method according to claim 7, wherein the guide tube further comprises a third connecting terminal for disposing a sampling head thereon.

9. The syringing method according to claim 8, wherein the first connecting terminal, the second connecting terminal and the third connecting terminal are communicated with each other.

10. The syringing method according to claim 8, wherein a waveform convergence hole is located between the first connecting terminal and the third connecting terminal.

* * * * *